United States Patent [19]

Kitao et al.

[11] 4,338,306
[45] Jul. 6, 1982

[54] ADJUVANT FOR PROMOTING ABSORPTION OF PHARMACOLOGICALLY ACTIVE SUBSTANCES THROUGH THE RECTUM

[75] Inventors: Kazuhiko Kitao; Ken-ichi Nishimura, both of Kyoto, Japan

[73] Assignee: Kyoto Yakuhin Kogyo Kabushiki Kaisha, Kyoto, Japan

[21] Appl. No.: 149,132

[22] Filed: May 12, 1980

[30] Foreign Application Priority Data

May 10, 1979 [JP] Japan .................................. 54-57690
Mar. 19, 1980 [JP] Japan .................................. 55-35128

[51] Int. Cl.³ .................... A61K 31/43; A61K 31/54; A61K 37/26; A61K 47/00
[52] U.S. Cl. .................................. 424/178; 424/246; 424/271; 424/365; 424/DIG. 15
[58] Field of Search ............... 424/271, DIG. 15, 365, 424/178, 246

[56] References Cited

U.S. PATENT DOCUMENTS

| | | | |
|---|---|---|---|
| 1,499,348 | 7/1924 | Crane et al. ............... | 424/DIG. 15 |
| 2,241,331 | 5/1941 | Shelton et al. ............. | 424/DIG. 15 |
| 2,854,378 | 9/1958 | Buckwalter ................ | 424/DIG. 15 |
| 4,250,169 | 2/1981 | Hosoi et al. ............... | 424/180 |

FOREIGN PATENT DOCUMENTS

| | | | |
|---|---|---|---|
| 2211619 | 9/1973 | Fed. Rep. of Germany ...... | 424/271 |
| 2853M | 10/1964 | France .................... | 424/271 |
| 2272684 | 1/1976 | France .................... | 424/271 |
| 792559 | 3/1958 | United Kingdom ............ | 424/271 |

OTHER PUBLICATIONS

Mima et al., C.A. vol. 80, (1974) #41050m.

*Primary Examiner*—Allen J. Robinson
*Attorney, Agent, or Firm*—Berman, Aisenberg & Platt

[57] ABSTRACT

Fatty acids having 8 to 14 carbon atoms, leucinic acid and nontoxic salts thereof promote the absorption of a pharmacologically-active substance through the rectum into the blood stream and effectively raise the concentration of such active substance in the blood stream even when said active substance is one which is usually absorbable through the rectum only with considerable difficulty.

12 Claims, No Drawings

ADJUVANT FOR PROMOTING ABSORPTION OF PHARMACOLOGICALLY ACTIVE SUBSTANCES THROUGH THE RECTUM

This invention relates to an adjuvant for promoting absorption of pharmacologically-active substances through the rectum; a rectal administration base composition comprising said adjuvant; and a pharmaceutical composition for rectal administration comprising said adjuvant, pharmacologically-active substances and base.

Pharmacologically-active substances which are hard to be absorbed into the circulation on oral administration are generally administered by parenteral routes. However, injections are accompanied by pain on the patient's part and are also inconvenient. Moreover, there are risks of muscular contracture. Thus, injections are not necessarily satisfactory. Even when a relatively readily absorbable species of pharmacologically active substances having antibiotic activity are administered by the oral route, a rapid drop of blood level is inevitable so that large or frequent doses must be essential. However, the unabsorbed residue will then have killing or static effects on bacteria in the intestine to upset the intestinal flora, thus causing clinically undesirable effects. Furthermore, many compounds are known to be decomposed, when orally administered, by digestive enzymes in the digestive tract.

Under the circumstances many attempts have been made to ensure an adequate absorption of pharmacologically-active substances into the living body. Any many of such attempts are aimed at rectal administration.

However, absorption-promoting adjuvants thus far known are not necessarily satisfactory, for some of them are not sufficiently effective in the promotion of absorption or unsatisfactory from the point of view of safety; others are only effective in the promotion of absorption of a very limited variety of pharmacologically-active substances, and still others have irritating effects on the rectal mucosa. Particularly, β-lactam antibiotics, such as penicillins, cephalosporins, etc., and high molecular weight peptides such as insulin etc., as such, are substantially not absorbed from the rectum and, although rectal preparations of these drugs have been attempted, these attempts have not proved fully successful as yet.

The present inventors conducted an intensive research under the above circumstances. The research led to the finding that (1) fatty acids having 8 to 14 carbon atoms, their nontoxic salts, leucinic acid and its nontoxic salts are capable of promoting absorption, from the rectum into the blood circulation, of a broad range of pharmacologically-active substances, particularly β-lactam compounds, such as penicillins and cephalosporins, and even high molecular weight peptides, such as insulin, and also that (2) the absorption promoting effects of these acids and their nontoxic salts are realized when they are incorporated at high concentrations in the preparations. The above finding was followed by further research which has resulted in the present invention.

This invention is therefore concerned with an absorption promoting adjuvant (for promoting absorption of pharmacologically-active substances from the rectum) which contains at least one member selected from the group consisting of fatty acids having 8 to 14 carbon atoms, leucinic acid and their nontoxic salts; a base for rectal preparation comprising 0.5 to 25 w/w % of at least one member selected from the group consisting of said acids and nontoxic salts; and a pharmaceutical composition comprising 0.5 to 20 w/w % of at least one member selected from the group consisting of said acids and their nontoxic salts, a suitable amount of a pharmacologically-active substance and a suitable amount of a base.

It is therefore an object of this invention to provide an adjuvant which promotes absorption of a pharmacologically-active substances through the rectum.

It is another object to provide an improved rectal base composition.

A further object of the invention is to provide a pharmaceutical composition for rectal administration, said composition being beneficial in that the pharmacological-active substance contained therein is readily absorbed into the blood stream through the rectum even when said active substance is usually absorbable through the rectum only with considerable difficulty.

Other objects will become apparent from the following description and claims.

The fatty acids having 8 to 14 carbon atoms which are employed in accordance with this invention may be naturally occurring acids or synthetic acids, although naturally occurring acids are generally preferred. Such fatty acids may be straight chain or branched chain, although straight chain species are preferred.

The number of carbon atoms in such fatty acids is desirably within the range of 8 to 12 (for example caprylic acid, capric acid, lauric acid, etc.) and, for still better results, 10 (such as capric acid).

The nontoxic salts to be employed in the present invention may be any salt which is pharmacologically acceptable. Examples of said salts are alkali metal salts (e.g. sodium salt, potassium salt), organic base salts (e.g. basic amino acid salts, such as arginine salt, lysine salt etc.), etc.

As the fatty acids, leucinic acid and nontoxic salts thereof there may be mentioned, by way of example, capric acid, its sodium, potassium, lysine and arginine salts; pelargonic acid, its sodium, lysine and arginine salts; caprylic acid, its sodium, potassium, lysine and arginine salts; undecylic acid and its arginine salt; lauric acid, its sodium, potassium, lysine and arginine salts; dodecylic acid and its lysine salt; myristic acid, its sodium, potassium, lysine and arginine salts; and leucinic acid, its sodium, potassium, lysine and arginine salts, preferably capric acid and its salts; lauric acid and its salts and; caprylic acid and its salts, more preferably capric acid and its salts.

These acids and nontoxic salts thereof may be used either alone or in combination.

The term "pharmacologically-active substances" as used throughout this specification means any and all substances which display pharmacological effects after absorption into the circulation. Since even those substances which cannot otherwise be absorbed when administered orally and have so far been only parenterally administered are absorbed readily from the rectum when the adjuvant of this invention is employed, the significance of the adjuvant of this invention lies in its application to such hardly absorbable pharmacologically-active substances. As specific examples of such pharmacologically-active substances there may be mentioned compounds containing a β-lactam ring (such as penicillins and cephalosporins) and peptide compounds, such as insulin.

The penicillins include ampicillin, ciclacillin cloxacillin, benzylpenicillin, carbenicillin, piperacillin, mezlocillin, pirbenicillin, ticarcillin, (2S, 5R, 6R)-6-[(R)-2-(4-hydroxy-1,5-naphthylidine-3-carboxamide)-2-phenylacetamide]-3,3-dimethyl-7-oxo-4-thia-1-azabicyclo [3. 2. 0]heptane-2-carboxylic acid and their salts, such as sodium salts, etc.

The cephalosporins include cephalothin, cefoxitin, cefazolin, cephaloridine, cephacetrile, cefotiam, ceforanide, cephanone, cefaclor, cefadroxil, cefatrizine, cefradine, cephaloglycin, 7-[D(−)-α-(-4-ethyl-2,3-dioxo-1-piperazinecarboxamide)-α-(4-hydroxyphenyl-)acetamide]-3-[(1-methyl-1H-tetrazole-5-yl)thiomethyl]-3-cepham-4-carboxylic acid (hereinafter referred to as T-1551), (6R, 7R)-[(Z)-2-methoxyimino-2-(2-imino-4-thiazoline-4-yl) acetamide]-8-oxo-5-thia-1-azabicyclo[4, 2, 0]oct-2-en-2-carboxylic acid (FK-749), (6R, 7R)-7-[2-carboxy-2-(4-hydroxyphenyl)acetamide]-7-methoxy-3-[(1-methyl-1H-tetrazol-5-yl-thio)methyl]-8-oxo-5-oxa-1-azabicyclo[4, 2, 0]oct-2-ene-2-carboxylic acid, 7-β-[2-(2-aminothiazol-4-yl)-(Z)-2-methoxyiminoacetamide]-3-[(1-methyl-1H-tetrazol-5-yl)thiomethyl]-ceph-3-ene-4-carboxylic acid, 7-(2-amino-2-phenylacetamide)-3-methoxy-8-oxo-5-thia-1-azabicyclo[4,2,0]oct-2-ene-2-carboxylic acid and their salts, such as sodium salts, etc.

The pharmaceutical composition for rectal administration in accordance with this invention is generally used as a rectal suppository or a preparation prepared by dispersing a pharmacologically-active substance, an adjuvant and other ingredients in a liquid oleaginous base to prepare a suspension or ointment and by filling the suspension or ointment in soft gelatin capsules or tubes.

These preparations can be manufactured by per se established pharmaceutical procedures. The base for rectal preparation according to this invention is one generally used in such preparations and, particularly, oleaginous and water-soluble bases are desirable for the purposes of this invention.

The oleaginous base includes, among others, such vegetable oils as peanut oil, olive oil, corn oil, fatty acid glyceride [e.g. Witepsol ® (Dynamite Nobel Chemicals), SB-Base ® (Kanegafuchi Chemical Co., Ltd.), O.D.O ® (Nisshin Oil K.K.), etc.] and such mineral oils as paraffin and vaseline.

The water-soluble base includes polyethylene glycol, propylene glycol, glycerin, etc.

The base of the present invention may be manufactured by dispersing said acid or its nontoxic salt in a base.

The pharmaceutical composition for rectal administration of the present invention may be manufactured in the following manner. First said acid or its salt is added to a base and, then, an effective amount of a pharmacologically-active substance is added and dispersed. The order of addition need not be limited to that described above, but may be reversed. It is also possible to incorporate an antioxidant, preservative, volume-builder, etc.

The level of addition of said fatty acid, leucinic acid or their nontoxic salts to the pharmaceutical composition for rectal administration is usually 0.5 to 20 w/w % on the whole preparation, preferably 1 to 15 w/w % and, for still better results, 3 to 10 w/w %. The level of addition of said acid or its nontoxic salt to the base is 0.5 to 25 w/w %, preferably 1 to 20 w/w % and still preferably 2 to 13 w/w %.

In preparing a pharmaceutical composition using the base for rectal preparation of this invention, the active substance is added to the base and, then as required, any other ingredients, such as an antioxidant, may further be added. It is advisable, therefore, to control the level of addition of said acid or its nontoxic salt to the base by predetermining the total level of addition of the pharmacologically-active substance and other ingredients. In such cases, adjustment should be made in such a manner that the concentration of said acid and/or nontoxic salt in the whole preparation (conventional base + pharmacologically-active substance + other ingredients + said acid and/or nontoxic salt) will be within the range of 0.5 to 20 w/w %, preferably 1 to 15 w/w % and still preferably 3 to 10 w/w %.

If the pharmacologically-active substance is, for example, an antibiotic, such as a β-lactam compound (such as penicillins, cephalosporins, etc.), it is added usually in the proportion of 20 to 500 mg and preferably 60 to 250 mg per gram of the whole preparation. In the case of insulin, etc., it is added usually in the proportion of 1 to 80 units, and preferably from 4 to 40 units, per gram of the whole preparation.

In accordance with the pharmaceutical composition of this invention, the dosage of an antibiotic, when a β-lactam antibiotic is used as said pharmacologically active substance, is 125 mg to 2 g (potency) per dose for adults and that of insulin is 1 to 100 units per dose for adults. The particle size of the nontoxic salts, and of the pharmacologically-active substance, is preferably not more than 100 mesh.

The fatty acids of 8 to 14 carbon atoms are generally known compounds and can be obtained by per se known procedure, such as hydrolysis of natural oil or the general processes for the production of carboxylic acids.

The nontoxic salts of such fatty acids are also generally known and can be prepared, for example, by allowing an alkali metal or an organic base to act on such fatty acids. Leucinic acid and its nontoxic salts are also generally known.

EXAMPLE 1

8.25 Grams of Witepsol H-15 (a registered mark of Dynamite Nobel) is melted at a temperature not exceeding 40° C. and 0.50 g of sodium caprate of 100 mesh pass is added and evenly dispersed by stirring. Then, 1.25 g (potency) of sodium ampicillin (hereinafter referred to briefly as AM-Na) of 100 mesh pass is evenly dispersed. The mixture is molded in suppository containers at the rate of one gram per container to prepare a rectal suppository.

EXAMPLE 2

Rectal suppositories of the compositions indicated in Table 1 were prepared in accordance with the procedure of Example 1. In Table 1 "Na" indicates sodium salt.

TABLE 1

| No. | Acids | Pharmacologically-active substance | Base |
|---|---|---|---|
| 1 | Capric acid-Na 5% | | |
| 2 | Lauric acid-Na 5% | 125 mg (potency) (13.3%) | Witepsol H-15 817 mg (81.7%) |
| 3 | Myristic acid-Na 5% | | |
| 4 | l-Arginine caprate | AM-Na | Witepsol H-15 |

TABLE 1-continued

| No. | Acids | Pharmacologically-active substance | Base |
|---|---|---|---|
| | 10% | 125 mg (potency) (13.3%) | 767 mg (76.7%) |
| 5 | l-Lysine caprate 10% | AM-Na 125 mg (potency) (13.3%) | Witepsol H-15 767 mg (76.7%) |
| 6 | Capric acid-Na 5% | Cefazolin-Na 125 mg (potency) (13.1%) | Witepsol H-15 819 mg (81.9%) |
| 7 | l-Arginine caprate 5% | | |
| 8 | Capric acid-Na 5% | Cephalothin-Na 125 mg (potency) (13.2%) | Witepsol H-15 818 mg (81.8%) |
| 9 | Capric acid-Na 5% | AM-Na 125 mg (potency) (13.3%) | O.D.O: 817 mg (81.7%) |

*Medium chain triglyceride

The absorption of the rectal suppositories prepared in Examples 1 and 2 into the circulation was determined from plasma concentrations (μg potency/ml) of pharmacologically active substance.

The results are shown in Table 2.

Method of determination:

From the anus of a dog fasted 24 hours, the composition was administered to a depth of about 3 cm.

To measure blood levels, blood samples were taken from the carotid vein at timed intervals and the plasma specimens prepared in the routine manner were assayed for titers of activity by the biological assay procedure.

Thus, in conformity with the Japan Antibiotic Standards, *Sarcina lutea* and *Bacillus subtilis* were used as assay organisms for penicillins and cephalosporins, respectively, and the assays were performed by the paper disk method (cultivation at 37° C. for 15 to 20 hours).

TABLE 2

Concentration of Pharmacologically-Active Substances in Plasma (Dog)

| Sample | Concentration in Plasma (μg potency/ml) | | | | |
|---|---|---|---|---|---|
| | 10 min. | 20 min. | 40 min. | 60 min. | 90 min. |
| Example 1 | 3.1 | 2.2 | 1.6 | 1.1 | 0.5 |
| Example 2 : No.1 | 8.0 | 6.5 | 2.7 | 1.4 | 0.6 |
| Example 2 : No.2 | 5.1 | 2.5 | 1.3 | 0.8 | 0.3 |
| Example 2 : No.3 | 0.5 | 1.5 | 0.3 | 0.1 | 0 |
| Example 2 : No.4 | 10.9 | 8.6 | 6.2 | 2.9 | 1.7 |
| Example 2 : No.5 | 9.2 | 7.0 | 2.9 | 1.6 | 0.7 |
| Example 2 : No.6 | 14.1 | 14.6 | 11.5 | 8.6 | 5.0 |
| Example 2 : No.7 | 13.0 | 10.4 | 5.4 | 4.9 | 3.2 |
| Example 2 : No.8 | 13.4 | 7.7 | 4.8 | 1.4 | 0.3 |
| Example 2 : No.9 (Control) | 8.2 | 8.8 | 4.2 | 2.1 | 0.8 |
| AM—Na 125 mg (Potency) (13.3%) Witepsol H-15 867 mg | 0 | 0 | 0 | 0 | 0 |

EXAMPLE 3

Rectal suppositories of the compositions indicated in the Sample column of Table 3 were prepared in accordance with the procedure of Example 1. These suppositories were administered to healthy adult male humans and the urinary excretions of the pharmacologically-active substances were determined. The results are shown in Table 3.

To measure the urinary excretions, urine samples were collected after administration at timed intervals, diluted and assayed by the procedure described in Example 2.

The urinary excretion values in Table 3 are percents based on the dose administered.

TABLE 3

Urinary Excretions of Pharmacologically-Active Substances (Human)

| Sample Pharmacologically-active substance . Base | Acid | Urinary excretions (% dose) | | | |
|---|---|---|---|---|---|
| | | 0–2hr | 2–4hr | 4–6hr | Total (0–6hr) |
| Ampicillin—Na 125 mg (potency) Witepsol H-15 Amount to make total preparation 1 g | — | 1.5 | 0.2 | 0 | 1.7 |
| | Sodium caprylate 5% | 12.8 | 0.8 | 0 | 13.6 |
| | Sodium caprate 1% | 8.4 | 1.9 | 0.2 | 10.5 |
| | Sodium caprate 5% | 24.0 | 4.0 | 1.4 | 29.4 |
| | Sodium caprate 10% | 32.6 | 4.0 | 1.5 | 38.1 |
| | Sodium laurate 5% | 18.9 | 2.2 | 0.8 | 21.9 |
| Cephalothin—Na 250 mg (potency) Witepsol H-15 Amount to make total preparation 1 g | — | 0 | 0 | 0 | 0 |
| | Sodium caprate 5% | 14.2 | 0.3 | 0 | 14.5 |
| | l-lysine caprate 10% | 22.5 | 0.6 | 0 | 23.1 |
| Cephalexin 125 mg (potency) Witepsol H-15 825 mg | Sodium caprate 5% | 31.0 | 4.4 | 0 | 35.4 |
| Cefazolin—Na 125 mg (potency) Witepsol H-15 Amount to make total preparation 1 g | Sodium caprate 5% | 18.2 | 6.6 | 3.8 | 28.6 |
| | Sodium laurate 5% | 10.2 | 4.5 | 1.0 | 15.7 |
| Ceftezole—Na 125 mg (potency) Witepsol H-15 819 mg | Sodium caprate 5% | 37.3 | 3.8 | 0.4 | 41.5 |
| Cefmetazole—Na 125 mg (potency) Witepsol H-15 819 mg | Sodium caprate 5% | 27.5 | 4.7 | 1.4 | 33.6 |
| Cephapirin—Na 125 mg (potency) | Sodium caprate 5% | 16.7 | 0.6 | 0.1 | 17.4 |

TABLE 3-continued
Urinary Excretions of Pharmacologically-Active Substances (Human)

| Sample Pharmacologically-active substance . Base | Acid | Urinary excretions (% dose) 0-2hr | 2-4hr | 4-6hr | Total (0-6hr) |
|---|---|---|---|---|---|
| Witepsol H-15 818 mg FK-749 125 mg (potency) | Sodium caprate 5% | 27.7 | 9.5 | 3.1 | 40.3 |
| Witepsol H-15 818 mg Cefotaxime Na 125 mg (potency) | Sodium caprate 5% | 26.1 | 1.4 | 0.3 | 27.8 |
| Witepsol H-15 818 mg Cefsulodin—Na 125 mg (potency) | Sodium caprate 5% | 9.0 | 2.1 | 0 | 11.1 |
| Witepsol H-15 820 mg Cefamandole—Na 125 mg (potency) | Sodium caprate 5% | 26.2 | 1.8 | 0.5 | 28.5 |
| Witepsol H-15 819 mg Sulbenicillin—Na 125 mg (potency) | Sodium caprate 5% | 21.0 | 4.6 | 0 | 25.6 |
| Witepsol H-15 812 mg Amoxicillin 125 mg (potency) | Sodium caprate 5% | 15.9 | 3.0 | 0.4 | 19.3 |
| Witepsol H-15 806 mg Dicloxacillin Na 125 mg (potency) | Sodium caprate 5% | 9.4 | 2.4 | 1.5 | 13.3 |
| Witepsol H-15 814 mg Cefoxitin Na 125 mg (potency) | Sodium caprate 5% | 18.7 | 1.4 | 0 | 20.1 |
| Witepsol H-15 819 mg Cefuroxime Na 125 mg (potency) | Sodium caprate 5% | 13.8 | 3.4 | 0.7 | 17.9 |
| Witepsol H-15 819 mg T-1551 Na 125 mg (potency) Witepsol H-15 821 mg | Sodium caprate 5% | 5.0 | 1.5 | 0 | 6.5 |

In Table 3 "Na" indicates sodium salt.

EXAMPLE 4

Rectal suppositories of the compositions indicated in the sample column of Table 4 were prepared in accordance with the procedure described in Example 1.

These rectal suppositories were administered to rabbits and the time courses of blood glucose levels were observed against controls where rectal suppositories containing none of the acids were administered. The results are set forth in Table 4.

Method of determination:

Each rectal suppository was administered to a depth of 2 cm from the anus of a rabbit fasted 24 hours. To measure blood glucose levels, blood samples were taken from the auricular vein at timed intervals and assayed by the glucose oxidase method.

TABLE 4
Blood Glucose level after Insulin Administration (Rabbit)

| No. | Sample Insulin . Base | Acid | Blood glucose level 0 hr. | 0.5 hr. | 1.0 hr. | 1.5 hr. | 2 hr. |
|---|---|---|---|---|---|---|---|
| 1 | Insulin 12 I.U. Witepsol H-15 569.5 mg | Sodium caprate 30 mg (5%) | 100% | 41% | 35% | 35% | 44% |
| 2 | Insulin 12 I.U. Witepsol H-15 569.5 mg | Sodium laurate 30 mg (5%) | 100% | 69% | 48% | 50% | 60% |
| 3 | Insulin 6 I.U. Witepsol H-15 569.5 mg (Control) | Leucinic acid 30 mg (5%) | 100% | 75% | 97% | 101% | 101% |
| | Insulin 12 I.U. | — | 100% | 105% | 103% | 95% | 106% |

TABLE 4-continued

| | Blood Glucose level after Insulin Administration (Rabbit) | | | | | | |
|---|---|---|---|---|---|---|---|
| | Sample | | | Blood glucose level | | | |
| No. | Insulin . Base | Acid | 0 hr. | 0.5 hr. | 1.0 hr. | 1.5 hr. | 2 hr. |
| | Witepsol H-15 599.5 mg | | | | | | |

What we claim is:

1. A rectally-administrable pharmaceutical composition which comprises:
   (a) an effective amount of at least one pharmaceutically-active component selected from the group consisting of a penicillin, a cephalosporin and insulin and
   (b) a sufficient amount of an adjuvant selected from the group consisting of a fatty acid having from 8 to 12 carbon atoms, leucinic acid and a nontoxic salt of either to promote absorption of the pharmaceutically-active component from the rectum into blood circulation.

2. A composition according to claim 1 wherein the pharmaceutically-active component comprises a penicillin.

3. A composition according to claim 1 wherein the pharmaceutically-active component comprises a cephalosporin.

4. A composition according to claim 1 wherein the pharmaceutically-active component comprises insulin.

5. A composition according to claim 1 in unit-dosage form and having a base suitable for rectal administration.

6. A composition according to claim 5 wherein the adjuvant comprises at least one acid selected from the group consisting of capric acid, caprylic acid and lauric acid or nontoxic salt thereof.

7. A composition according to claim 6 wherein the adjuvant comprises a capric acid alkali-metal salt.

8. A composition according to one of claims 5 to 7 wherein the pharmaceutically-active component comprises at least one member selected from the group consisting of a penicillin and a cephalosporin.

9. A composition according to one of claims 5 to 7 in suppository form.

10. A composition according to one of claims 5 to 7 and having from 0.5 to 25 w/w percent of said adjuvant.

11. A method for promoting absorption of a rectally-absorbable pharmacologically-active substance through the rectum into the blood stream which comprises rectally administering an effective amount of the pharmacologically-active substance with an absorption-promoting amount of adjuvant comprising at least one member selected from the group consisting of:
    (a) a fatty acid having from 8 to 12 carbon atoms,
    (b) leucinic acid and
    (c) a nontoxic salt of (a) or (b);
the pharmacologically-active substance comprising at least one member selected from the group consisting of a penicillin, a cephalosporin and insulin.

12. A method according to claim 11 wherein the pharmacologically-active substance comprises at least one member selected from the group consisting of a penicillin and a cephalosporin.

* * * * *